United States Patent [19]
Martell

[11] Patent Number: 6,007,525
[45] Date of Patent: Dec. 28, 1999

[54] FILTERING AND DEODORIZING DEVICE FOR USE WITH COLOSTOMY POUCH

[76] Inventor: Joseph A. Martell, 517-20th Avenue, Deux-Montagnes, Quebec, Canada, J7R 4G9

[21] Appl. No.: 08/902,224

[22] Filed: Jul. 29, 1997

[30] Foreign Application Priority Data

May 30, 1997 [CA] Canada .................................. 2206612

[51] Int. Cl.⁶ .............................................. A61F 5/44
[52] U.S. Cl. .......................................... 604/333; 604/335
[58] Field of Search .................................. 604/332–345, 604/277; 55/385.4; 96/132, 134

[56] References Cited

U.S. PATENT DOCUMENTS

| | | | |
|---|---|---|---|
| 4,746,338 | 5/1988 | Williams | 55/275 |
| 4,863,447 | 9/1989 | Smith | 604/335 |
| 5,316,569 | 5/1994 | Heunermund | 96/134 |
| 5,688,256 | 11/1997 | Surratt et al. | 604/333 |
| 5,728,080 | 3/1998 | Suyama | 604/333 |

FOREIGN PATENT DOCUMENTS

| | | | |
|---|---|---|---|
| 3608933 | 10/1987 | Germany | 604/333 |
| 2078128A | 1/1982 | United Kingdom | 96/132 |

OTHER PUBLICATIONS

Convatec/Squibb, Advertising Leaflet on "Hollister Ostomy Products".

Primary Examiner—John G. Weiss
Assistant Examiner—Dennis Ruhl
Attorney, Agent, or Firm—Swabey Ogilvy Renault

[57] ABSTRACT

The invention relates to a filtering and deodorizing device for use with a colostomy pouch. The device of the invention comprises a housing having first and second chambers in gas flow communication with one another; gas inlet means adapted for connection to the colostomy pouch, for introducing into the first chamber gas flowing from the pouch; filtering means in the first chamber for filtering gas flowing through the inlet means; deodorizing means in the second chamber for deodorizing the filtered gas flowing from the first chamber; gas control means positioned downstream of the deodorizing means and operative between open and closed positions for regulating gas build-up in the pouch; and gas outlet means for discharging the gas flowing from the second chamber when the gas control means is in the open position. Gas build-up in the pouch is released when the gas control means is in the open position so that the gas flows from the pouch through the first chamber and then through the second chamber and is evacuated as a filtered and deodorized gas through the gas outlet means.

20 Claims, 3 Drawing Sheets

FILTERING AND DEODORIZING DEVICE FOR USE WITH COLOSTOMY POUCH

BACKGROUND OF THE INVENTION

The present invention pertains to improvements in the field of colostomy products. More particularly, the invention relates to a filtering and deodorizing device for use with a colostomy pouch.

Colostomy is the surgical formation of an artificial anus by making an opening from the colon through the abdominal wall. A person having undergone colostomy must constantly keep a colostomy pouch in position against such an opening or stoma by means of a flange attachment to receive feces discharged through the stoma. An abdominal belt support placed over the colostomy pouch is generally used to hold the pouch in position. When such a belt is used, the person cannot release gas build-up accumulated in the closed pouch unless the pouch is disconnected from the flange surrounding the stoma, which can only be accomplished by the removal of clothing and the belt.

Since 1990, colostomy pouches have been provided with perforations defining a vent for gas buildup release. However, there is no control of the gas release which provides an offensive odor. With no control of the gas release, the pouch will completely deflate and come into contact with the stoma. The pouch touching the stoma causes the puddling and accumulation of discharged feces around the attachment flange. The accumulation of feces, on the other hand, causes irritation of the skin around the stoma if the feces are not removed and the skin washed.

Because a gas release problem can occur at the most unexpected moment, many persons have been using colostomy pouches without the above vent, thereby trapping the gas. The person must then retreat to a private room to disconnect the pouch so as to allow the release of the trapped gas. This procedure requires of course the removal of the person's clothing to gain access to the pouch.

SUMMARY OF THE INVENTION

It is therefore an object of the present invention to overcome the above drawbacks and to provide a filtering and deodorizing device for use with a colostomy pouch, which allows one to regulate gas build-up in the pouch and to provide a controlled release of filtered and deodorized gas.

In accordance with the present invention, there is a filtering and deodorizing device for use with a colostomy pouch, comprising:

a housing having first and second chambers in gas flow communication with one another;

gas inlet means adapted for connection to the colostomy pouch, for introducing into the first chamber gas flowing from the pouch;

filtering means in the first chamber for filtering gas flowing through the inlet means;

deodorizing means in the second chamber for deodorizing the filtered gas flowing from the first chamber;

gas control means positioned downstream of the deodorizing means and operative between open and closed positions for regulating gas build-up in the pouch; and gas outlet means for discharging the gas flowing from the second chamber when the gas control means is in the open position.

Gas build-up in the pouch is released when the gas control means is in the open position so that the gas flows from the pouch through the first chamber and then through the second chamber and is evacuated as a filtered and deodorized gas through the gas outlet means.

BRIEF DESCRIPTION OF THE DRAWINGS

Further features and advantages of the invention will become more readily apparent from the following description of preferred embodiments as illustrated by way of examples in the accompanying drawings, in which.

DESCRIPTION OF PREFERRED EMBODIMENTS

Figure 1:
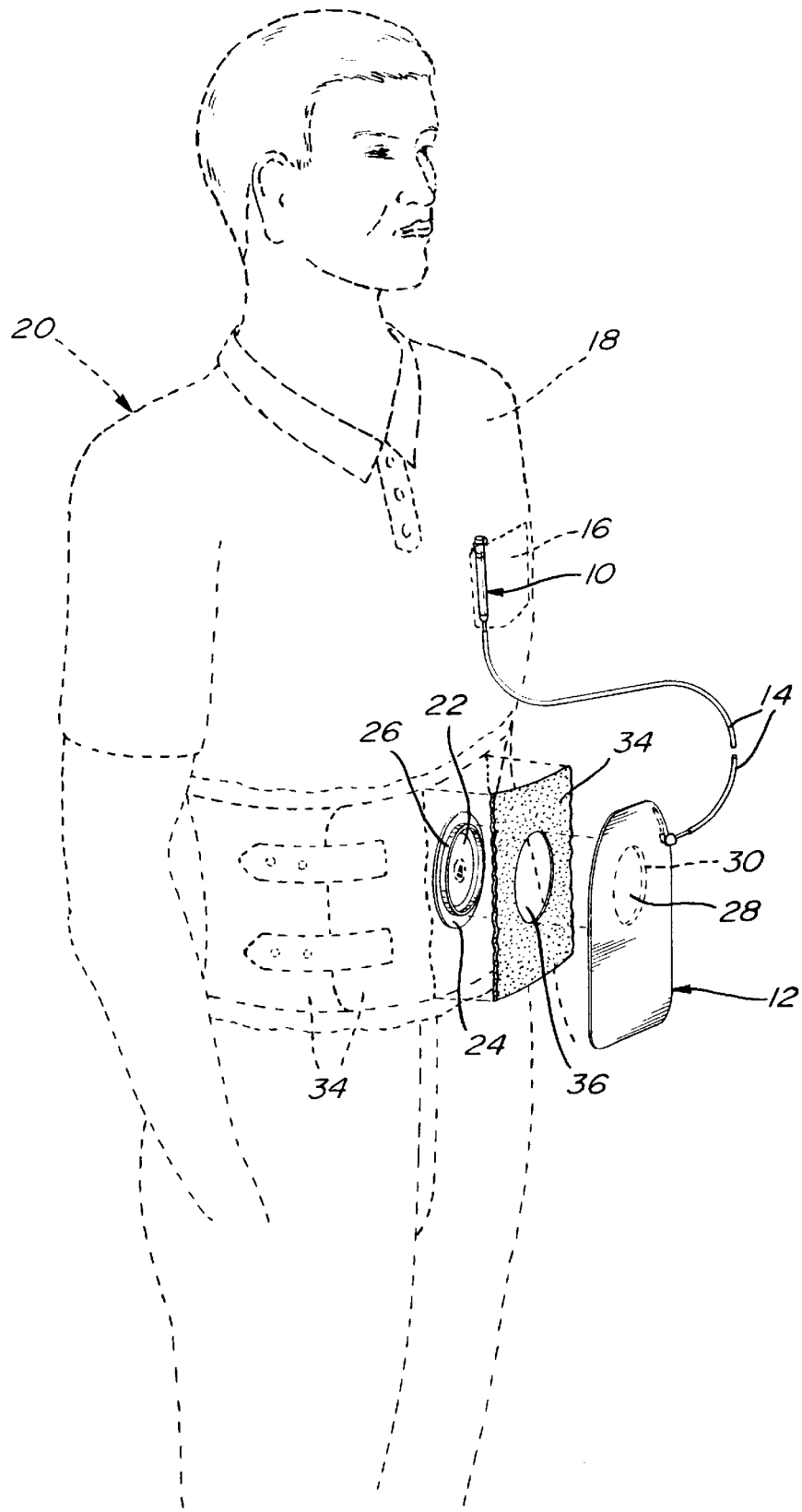
FIG. 1 is an exploded perspective view showing how a filtering and deodorizing device according to the invention is used with a colostomy pouch for regulating gas build-up therein and permitting the release of a filtered and deodorized gas.

Referring first to FIG. 1, there is illustrated a filtering and deodorizing device which is generally designated by reference numeral 10 and shown connected to a colostomy pouch 12 by means of a transparent flexible conduit 14 providing gas flow communication between the device 10 and the interior of the pouch 12. The device 10 can be conveniently attached to the pocket 16 of a skirt 18 worn by the person 20 having undergone colostomy and provided with a stoma 22 at the abdomen. A circular flange 24 having a circumferential lip 26 surrounds the stoma 22. The pouch 12 is provided with an opening 28 through which pass the feces discharged from the stoma 22. A generally circular flange 30 having a circumferential groove 32 (shown in FIG. 2) surrounds the opening 28, the groove 32 receiving the lip 26 in snap-fit engagement. As shown, an abdominal belt 34 extending around the waist is interposed between the person's body and the pouch 12, the belt 34 having an opening 36 through which the lip 26 extends.

Figure 2:
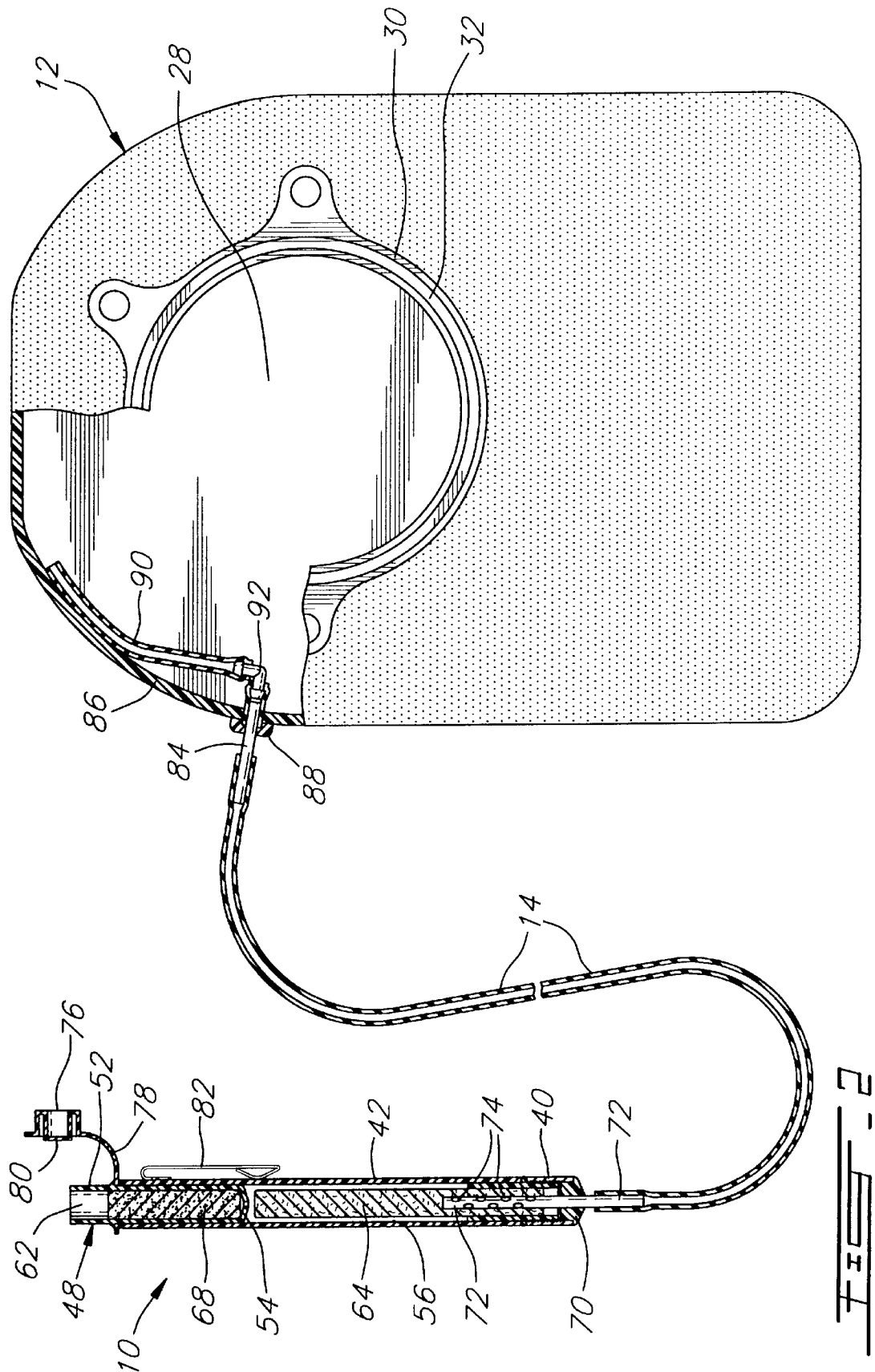
FIG. 2 is a part-sectional rear elevation view of the colostomy pouch shown in FIG. 1, equipped with the filtering and deodorizing device of the invention.
Figure 3:
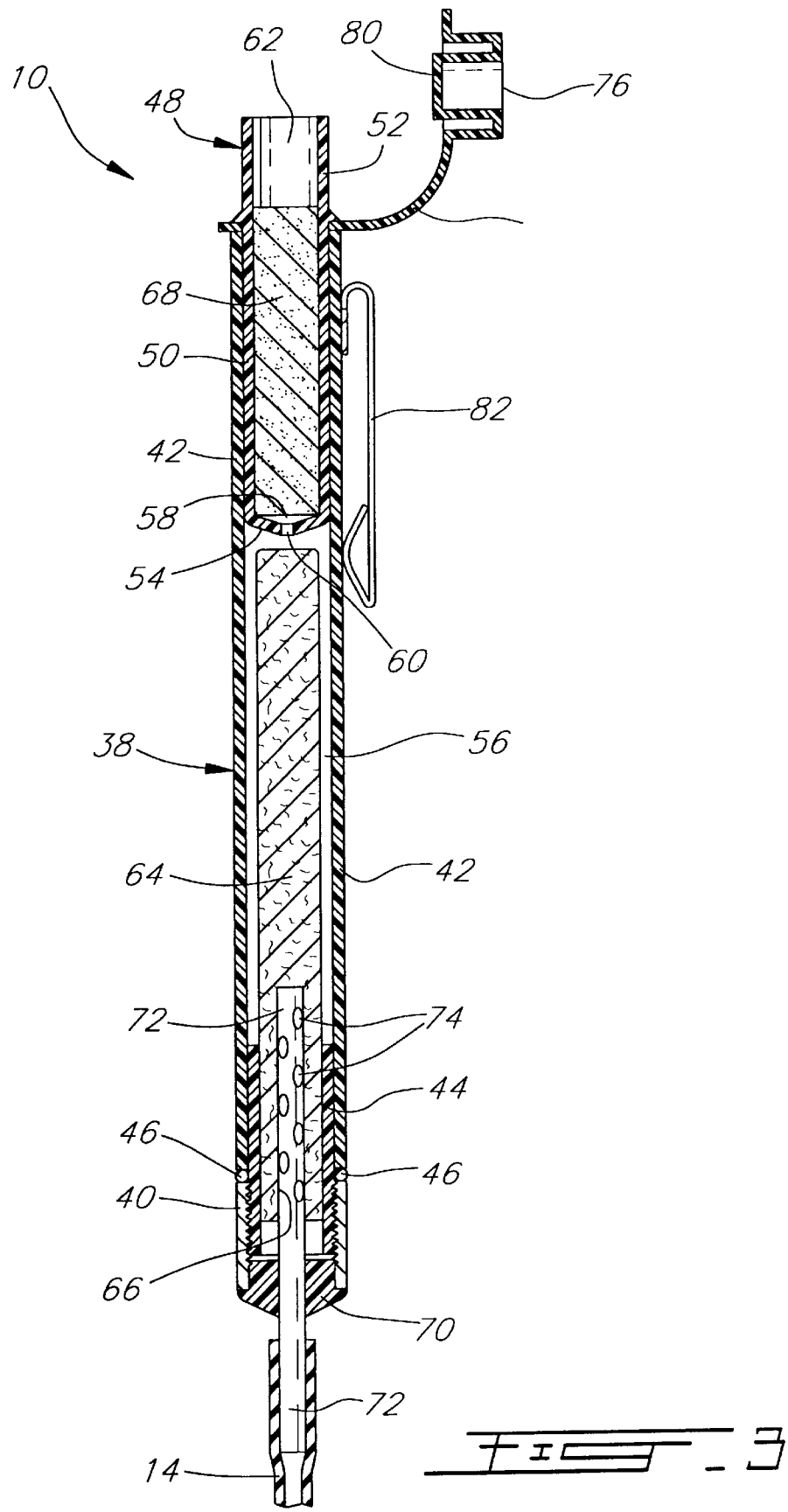
FIG. 3 is a longitudinal sectional view of the filtering and deodorizing device shown in FIGS. 1 and 2.

As shown in FIGS. 2 and 3, the filtering and deodorizing device 10 comprises a cylindrical housing 38 having first and second coaxially extending sections 40,42 which are detachably connected to one another by means of an inner coupling member 44. Member 44 is fixed to the section 42 and has a threaded portion extending beyond the lower extremity of section 42 and threadably engaging the section 40. A resilient O-ring 46 extends around the coupling member 44 and the sections 40,42 for providing a gas-tight connection. The device 10 further includes a cylindrical insert member 48 having a first portion 50 extending coaxially into the second section 42 and fixed thereto, and a second portion 52 projecting upwardly therefrom. The first portion 50 has a lower end wall 54 constituting a partition defining on either side thereof first and second chambers 56,58. The wall 54 has an aperture 60 formed therethrough for providing gas flow communication between the chambers 56,58. The second portion 52 is provided with a gas discharge opening 62. A disposable, elongated filter cartridge 64 having a longitudinally extending blind-bore 66 formed therein is disposed in the chamber 56. A porous element 68 made of foam material and impregnated with a deodorizing liquid is disposed in the chamber 58. The sections 40,42 and insert member 48 have a circular cross-section.

The section 40 has a lower end wall 70 through which extends a tubular gas inlet member 72 connected to the conduit 14. The inlet member 72 partially extends into the chamber 56 and has a portion extending into the blind-bore 66 of the filter cartridge 64. The portion which extends into the blind-bore 66 is provided with lateral perforations 74.

A closure member 76 in the form of a cap is provided at the upper end of the device 10. The closure member 76 is hingedly connected to the second 42 by means of a flexible hinge element 78, for movement between a closed position whereat the closure member 76 closes the opening 62 and an open position whereat the closure member 76 permits a gas discharge from the chamber 58. The closure member 76 is a sealing plug 80 for sealingly closing the opening 62. The sealing plug 80 is adapted to penetrate into the opening 62 and sealingly engage the portion 52 of insert member 48, when the closure member 76 is moved to the closed position. A clip member 82 fixed to the section 42 is provided for releasably attaching the device 10 to the pocket 16 (shown in FIG. 1) of the person's shirt 18.

As shown in FIG. 2, the colostomy pouch 12 is provided with a tubular gas outlet member 84 which extends through the wall 86 of the pouch 12 and is secured thereto by means of adhesive 88. The conduit 14 is connected to the outlet member 84. An upwardly extending conduit 90 disposed in the pouch 12 and adjacent the wall 86 thereof is connected to the outlet member 84 by means of an elbow coupling 92. The conduit 90 opens into the upper portion of the pouch 12 for collecting gas therefrom.

Gas build-up in the pouch 12 is regulated by opening or closing the closure member 76. Uncomfortable gas build-up can thus be released by opening the closure member 76 so that the gas collected by the conduit 90 and flowing through the conduit 14 passes through the inlet member 72, then through the chamber 56 where it is filtered by the filter cartridge 64 and thereafter through the chamber 58 where it is deodorized by the porous element 68 impregnated with deodorizing liquid. The filtered and deodorized gas is finally evacuated through the gas discharge opening.

I claim:

1. A filtering and deodorizing device for use with a colostomy pouch, comprising:
    a housing having first and second chambers in gas flow communication with one another;
    gas inlet means adapted for connection to said colostomy pouch, for introducing into said first chamber gas flowing from said pouch;
    filtering means in said first chamber for filtering gas flowing through said inlet means;
    deodorizing means in said second chamber for deodorizing the filtered gas flowing from said first chamber;
    gas control means positioned downstream of said deodorizing means and operative between open and closed positions for regulating gas build-up in said pouch; and
    gas outlet means for discharging the gas flowing from said second chamber when said gas control means is in said open position;
    whereby, when said gas inlet means is connected to said colostomy pouch, gas buildup in said pouch is released when said gas control means is in said open position, the gas flowing from said pouch through said first chamber and then through said second chamber and being evacuated as a filtered and deodorized gas through said gas outlet means,
    wherein said device further includes releasable attachment means for releasably attaching said housing to a garment of a person provided with said colostomy pouch.

2. A device as claimed in claim 1, wherein said housing is cylindrical and comprises first and second coaxially extending sections detachably connected to one another, and wherein said first and second chambers are defined in said second section, said first section being provided with said gas inlet means.

3. A device as claimed in claim 2, wherein said second section is provided therein with a partition defining on either side thereof said first and second chambers, said partition having an aperture formed therethrough and providing said gas flow communication between said first and second chambers.

4. A device as claimed in claim 2, further including sealing means disposed between said first and second sections for providing a gas-tight connection therebetween.

5. A device as claimed in claim 4, wherein said sealing means comprises an O-ring.

6. A device as claimed in claim 2, wherein said filtering means comprises a disposable, elongated filter cartridge.

7. A device as claimed in claim 6, wherein said filter cartridge has a longitudinally extending blind-bore formed therein.

8. A device as claimed in claim 7, wherein said first section has an end wall and wherein said inlet means comprises a tubular inlet member extending through said end wall and partially into said first chamber, said inlet member having a portion extending into the blind-bore of said filter cartridge, and an elongated conduit having one end connected to said inlet member and an opposite end adapted for connection to gas discharge means of said pouch.

9. A device as claimed in claim 8, wherein said gas discharge means comprises a tubular outlet member secured to said pouch and opening thereinto.

10. A device as claimed in claim 9, wherein said pouch is elongated and extends substantially vertically, and wherein said outlet member has a portion extending into said pouch, said gas discharge means further including an upwardly extending conduit having a lower end connected to said portion of said outlet member and an upper end opening into an upper portion of said pouch.

11. A device as claimed in claim 8, wherein the portion of said inlet member extending into said blind-bore is provided with a plurality of lateral perforations.

12. A device as claimed in claim 3, wherein said deodorizing means comprises a porous element impregnated with a deodorizing liquid.

13. A device as claimed in claim 12, wherein said porous element is made of a foam material.

14. A device as claimed in claim 12, further including a cylindrical insert member having a first portion coaxially extending into said second section and a second portion projecting outwardly therefrom, and wherein said first portion has an apertured end wall constituting said partition with said second chamber being defined in said first portion and containing said porous element, and said second portion has a gas discharge opening defining said gas outlet means.

15. A device as claimed in claim 14, wherein said gas control means comprises a closure member hingedly connected to said second section for movement between said closed position whereat said closure member closes said gas discharge opening and said open position whereat said closure member permits evacuation of said filtered and deodorized gas.

16. A device as claimed in claim 15, wherein said closure member is provided with sealing means for sealingly closing said gas discharge opening.

17. A device as claimed in claim 16, wherein said sealing means comprises a sealing plug adapted to penetrate into said gas discharge opening and sealingly engage the second portion of said insert member when said closure member is moved to said closed position.

18. A device as claimed in claim 14, wherein said first and second sections and said insert member have a circular cross-section, and wherein said housing has the general form of a pen.

19. A device as claimed in claim 1, wherein said releasable attachment means comprises a clip member fixed to said housing.

20. A filtering and deodorizing device for use with a colostomy pouch, comprising:

a housing having first and second chambers in gas flow communication with one another;

gas inlet means adapted for connection to said colostomy pouch, for introducing into said first chamber gas flowing from said pouch;

filtering means in said first chamber for filtering gas flowing through said inlet means;

deodorizing means in said second chamber for deodorizing the filtered gas flowing from said first chamber;

gas control means positioned downstream of said deodorizing means and operative between open and closed positions for regulating gas build-up in said pouch; and gas outlet means for discharging the gas flowing from said second chamber when said gas control means is in said open position;

whereby, when said gas inlet means is connected to said colostomy pouch, gas build-up in said pouch is released when said gas control means is in said open position, the gas flowing from said pouch through said first chamber and then through said second chamber and being evacuated as a filtered and deodorized gas through said gas outlet means, wherein said housing is cylindrical and comprises first and second coaxially extending sections detachably connected to one another, and wherein said first and second chambers are defined in said second section, said first section being provided with said gas inlet means; and wherein said second section is provided therein with a partition defining on either side thereof said first and second chambers, said partition having an aperture formed therethrough and providing said gas flow communication between said first and second chambers.

* * * * *